United States Patent
da Silva Junior et al.

(10) Patent No.: US 7,251,384 B2
(45) Date of Patent: Jul. 31, 2007

(54) OPTICAL FIBER PH SENSOR

(75) Inventors: Manoel Feliciano da Silva Junior, Rio de Janeiro (BR); Arnaldo Rodrigues D'Almeida, Rio de Janeiro (BR); Fabio Pereira Ribeiro, Rio de Janeiro (BR); Luiz Carlos Guedes Valente, Rio de Janeiro (BR); Arthur Martins Barbosa Braga, Rio de Janeiro (BR); Adriana Lucia Cerri Triques, Rio de Janeiro (BR)

(73) Assignee: Petroleo Brasileiro S.A. - Petrobras, Rio de Janeiro (BR)

( * ) Notice: Subject to any disclaimer, the term of this patent is extended or adjusted under 35 U.S.C. 154(b) by 0 days.

(21) Appl. No.: 11/137,432

(22) Filed: May 26, 2005

(65) Prior Publication Data

US 2005/0265649 A1    Dec. 1, 2005

(30) Foreign Application Priority Data

May 31, 2004   (BR) .................................. 0404129

(51) Int. Cl.
*G02B 6/00* (2006.01)
(52) U.S. Cl. ........................................................ 385/13
(58) Field of Classification Search ..................... None
See application file for complete search history.

(56) References Cited

U.S. PATENT DOCUMENTS

| 5,015,843 | A | 5/1991 | Seitz et al. | |
|---|---|---|---|---|
| 6,965,708 | B2 * | 11/2005 | Luo et al. ...................... | 385/12 |
| 7,003,184 | B2 * | 2/2006 | Ronnekleiv et al. .......... | 385/12 |
| 2002/0041724 | A1 * | 4/2002 | Ronnekleiv et al. .......... | 385/12 |
| 2004/0022475 | A1 * | 2/2004 | Pennington ................... | 385/12 |

* cited by examiner

*Primary Examiner*—Sung Pak
(74) *Attorney, Agent, or Firm*—Sughrue Mion, PLLC

(57) ABSTRACT

An optical fiber pH sensor 100, 200, 300 is described, where a transducer mechanically couples a Bragg grating to a pH-sensitive hydrogel, said sensor comprising a central part 110, 210, 301 where are placed the optical fiber 121 containing a Bragg grating 122, the pH-sensitive hydrogel set of discs 130, and the mechanical transducer which is a spring 123 a beam 215 or still the optical fiber itself 121, the mechanical transducer assuring the strain on the Bragg grating 122. The change in hydrogel hydrodynamic volume resulting from a change of the pH of the medium introduces a force that is sufficient to cause a strain in the Bragg grating. The measure of the pH change is retrieved using the usual techniques for wavelength measurement. The pH sensor 100, 200, 300 of the invention is useful for the indirect evaluation and control of corrosion in petroleum wells and is suitable for multiplexing with other optical fiber sensors measuring the same or different parameters.

24 Claims, 11 Drawing Sheets

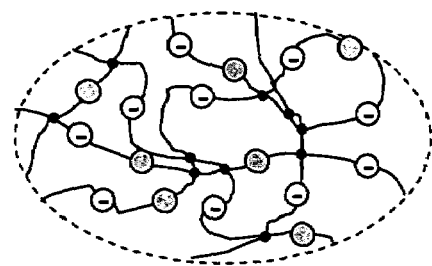
FIG. 1A
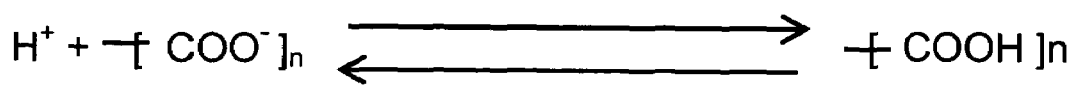
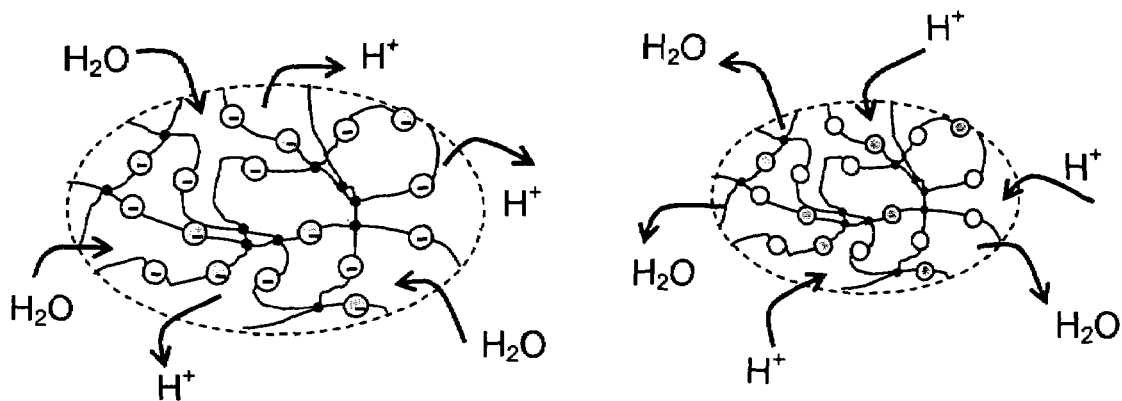
FIG. 1B          FIG. 1C

OPTICAL FIBER PH SENSOR

FIELD OF THE INVENTION

The present invention relates to an optical fiber pH sensor designed for measuring the pH of aqueous solutions, where a transducer mechanically couples a Bragg grating to a pH-sensitive hydrogel, more specifically, to a pH sensor where the change of the hydrogel hydrodynamic volume resulting from a pH change in the medium causes a force which is large enough to strain the Bragg grating, the pH measurement being retrieved through usual techniques for wavelength measurement.

BACKGROUND INFORMATION

A Fiber Bragg Grating or FBG is a passive optical component obtained by imprinting a local, longitudinal and periodic modulation of the refractive index of the optical fiber core. In view of the local change of the refractive index, any light propagating along the fiber core undergoes partial reflection at each of the grating layers. As a consequence of the periodicity of the index modulation, constructive interference of the reflected light occurs for the wave vectors that meet the Bragg condition $\lambda_B = 2n\Lambda$, where $\lambda_B$ is the wavelength at the peak of the reflected light spectrum, or Bragg wavelength, $\Lambda$ is the grating spatial periodicity, and n is the core refractive index. This implies that a portion of the incident spectrum is not transmitted, instead, it is reflected by the Bragg grating.

Since the wavelength reflected by the Bragg grating is a function of n and $\Lambda$, changes in temperature, $\Delta T$, or in the strain to which the grating is submitted, $\Delta\epsilon$, cause significant changes in these parameters, this leading to changes in the Bragg wavelength that can be set forth as $\Delta\lambda = \lambda_B(\alpha\Delta T + \beta\Delta\epsilon)$.

Bragg grating sensors are employed for the measurement of several physical and chemical parameters. The mechanisms employed in Bragg grating sensing are usually based on the transference to the fiber of a strain, the origin of which can be an elastic structure such as a spring or a diaphragm. The principle of operation of the FBG sensors consists of monitoring the Bragg wavelength changes, $\Delta\lambda$, and of correlating them to the changes in the mensurand value.

Good measurement resolution can be obtained according to the wavelength measurement instrumentation. If a wavelength measurement system providing ±1 pm uncertainty is employed, the FBG technique can provide resolutions as high as tenths of Celsius degrees and few μm/m for temperature and strain changes, respectively.

Hydrogels are made up of a combination of a solid crosslinked polymeric chain and a neighboring aqueous solution. Whenever stimulated for example by changes in temperature, electric and magnetic fields and pH of the medium, these materials can undergo a pronounced and reversible change in their hydrodynamic volume. The processes responsible for hydrodynamic volume change are governed by interactions between the polymeric network and the aqueous solution. In pH-sensitive gels, the amount of hydrodynamic volume change is governed by the equilibrium between the restoring force provided by the crosslinks and the osmotic force caused by the diffusion of ionic species. High Young modulus values have been experimentally predicted and observed for various hydrogels, and a variety of chemical-mechanical actuators have been built. To this respect, see the articles by Brock, D., Lee, W. J., Segalman, D., Witkowski, M., "A Dynamic-Model of a Linear-Actuator Based on Polymer Hydrogel", Journal of Intelligent Material Systems and Structures 5, 764 (1994); Shahinpoor, M., "Micro-electro-mechanics of Ionic Polymer Gels as Electrically Controllable Artificial Muscles", Journal of Intelligent Material Systems and Structures 6, 307 (1995); Woojin Lee, "Polymer Gel Based Actuator: Dynamic model of gel for real time control", PhD Thesis, MIT (1996); and Kato, N., Takizawa, Y., Takahashi, F., "Magnetically Driven Chemomechanical Device with Poly(N-Isopropylacrylamide) Hydrogel Containing Gamma-$Fe_2O_3$", Journal Of Intelligent Material Systems And Structures 8, 588 (1997).

In ionic polymers, the electrostatic repulsion between similar charges can considerably increase the swelling forces. The amount of repulsion depends on the number of charges and on the concentration of counter-ions present in the polymer. The increase in counter-ion concentration causes an increase of the charge shielding, this resulting in reduction of the repulsion forces. This phenomenon can also be envisaged as an osmotic pressure effect. The concentration of electric charges within the crosslinked polymer is higher than in the solvent. Therefore, the solvent enters the polymer in an attempt to equalize the osmotic pressure inside and outside the hydrogel.

For background information on pH-sensitive hydrogels see the articles by S. K. De et al., "Equilibrium Swelling and Kinetics of pH-responsive Hydrogels: Models, Experiments, and Simulations", Journal of Microelectromechanical Systems, 11, 544 (2002) and "A chemo-electro-mechanical mathematical model for simulation of pH sensitive hydrogels", Mechanics of Materials 36, 395 (2004); H. Li, T. Y. Ng, Y. K. Yew, K. Y. Lam, "Modeling and simulation of the swelling behavior of pH-stimulus-responsive hydrogels", Biomacromolecules 6, 109 (2005); Marra, S. P., Ramesh, K. T., Douglas, A. S., "Mechanical Characterization of Active Poly(vinyl alcohol)-Poly(acrylic acid) Gel", Materials Science and Engineering C 14, 25 (2001); Fei, J. Q., Gu, L. X., "PVA/PAA Thermo-crosslinking Hydrogel Fiber: Preparation and pH-sensitive Properties in Electrolyte Solution", European Polymer Journal 38, 1653 (2002); and Johnson, B., Niedermaier, D. J., Crone, W. C., Moorthy, J., Beebe, D. J., "Mechanical Properties of a pH Sensitive Hydrogel", Proceedings of the Annual Conference of the Society for Experimental Mechanics, Milwaukee, EUA, 2002; Marra, S. P., Ramesh, K. T., Douglas, A. S., "Mechanical Characterization of Active Poly(vinyl alcohol)-Poly(acrylic acid) Gel", Materials Science and Engineering C 14, 25 (2001).

U.S. Pat. No. 5,015,843 teaches a chemical sensor that can detect the presence of a chemical species in solution based on the swelling of a polymer upon reaction to the chemical species. The polymer swelling is indirectly determined by measuring the light reflected from a reflector directly or indirectly attached to the polymer. In this way, an increase or reduction of the polymer size changes the distance between the reflector and a source of light. Measurements of the intensity of light reflected by the reflector indicate the amount of swelling or shrinking of the polymer in response to the chemical species. However this U.S. patent does not aim to measure pH nor it makes use of a fiber Bragg grating as in the present invention.

In chemical processes pH is the most widely used chemical parameter and provides information on the concentration of hydrogen and hydroxyl ions in an aqueous solution. pH measures the ionic activity of hydrogen ions in solution. The concentration and ionic activity are related, and are the same for ionic solutions for which the dilution can be considered as infinite.

State-of-the-art pH measurements include pH indicators using dyes, the color of which is pH-dependent and the pH electrode, the working principle of which is the electrochemical cell. Non-conventional techniques include the ISFET (Ionic Selective Field Effect Transistor) and the optical sensors. In an optical sensor, the pH measurement is carried out by the modulation of the light intensity through absorption, reflection or fluorescence of hydrogen ion-sensitive chromophores.

On the other hand, certain drawbacks in the detection of metallic corrosion in difficult access equipment and installations have not yet been solved in the several industrial fields.

Sensors for evaluating corrosion are normally based on sacrificial bodies or on the monitoring of the cathodic reaction occurring concomitant to the oxidation process and corrosion reduction.

In the petroleum industry, metallic corrosion can cause the premature failure of equipments as well as oil leaks, leading to human and environment safety risk and with expensive maintenance operations. Real-time, dynamic knowledge of the conditions that generate metallic corrosion can be a very precious tool for the prevention and control of its consequences.

Much of the research on metallic corrosion applied to the petroleum industry is focused on the determination of the medium corrosiveness for the evaluation of material corrosion rates. The corrosion rate of most of metals is affected by pH. In general, the effect of pH on the corrosion rate follows three standards. According to the first of these standards, applicable to metals that are soluble in acid, such as iron, the corrosion rate is fairly high for pH<4, while for 4<pH<10, it depends on the concentration of oxidants. The second standard applies to metals such as aluminum and zinc, the corrosion rate of which is high for pH<4 and pH>8. Finally, noble metals, such as gold and platinum, are not affected by pH.

The correlations used for estimating pH in subsurface environments, based on measurements carried out at the surface, came out to be fairly imprecise. A sensor that could be installed downhole and in other sites of the oil production system would constitute a useful tool to check the correlations and would help the selection of the most suitable materials to be used in equipment and pipes.

The possibility to monitor, continuously and permanently, downhole parameters such as temperature (T), pressure (P) and flow rate in the petroleum wells is at the origin of what is presently called intelligent or smart wells.

Nowadays, sensors for downhole pressure, temperature and flow rate based on the FBG technique are operative. On this respect see the articles by A. D. Kersey, "Optical fiber sensors for permanent downwell monitoring applications in the oil and gas industry", IEICE Transactions on Electronics E83C, 400 (2000); and Ph. M. Nellen, P. Mauron, A. Frank, U. Sennhauser, K. Bohnert, P. Pequignot, P. Bodor, H. Brandle, "Reliability of fiber Bragg grating based sensors for downhole applications", Sensors Actuators A-Physical 103, 364 (2003).

However, there are still important downhole variables to be monitored, one of these being pH. Real-time pH measurement, together with pressure, temperature and flow rate, can provide a better understanding of the corrosion process and be useful to infer corrosion rate in oil plants.

Thus, it is clear that the technique still needs an optical fiber pH sensor where the volume change of a pH-sensitive hydrogel is transmitted to an optical fiber containing a Bragg grating, the induced strain variation changing the wavelength of the Bragg grating, yielding a pH sensor, such sensor being described and claimed in the present application.

SUMMARY OF THE INVENTION

Broadly, the present invention relates to a pH sensor for measuring the pH of aqueous solutions with the aid of an optical fiber, the sensor comprising a rigid housing containing a first compartment where is inserted a set of discs made up of a pH-sensitive hydrogel and, separated from the said first compartment by any device, a second compartment mechanically connected to the said first one and having an optical fiber containing a Bragg grating, said hydrogel undergoing a hydrodynamic volume change caused by a pH change, the strain induced by said volume change being transmitted to the Bragg grating so that the Bragg wavelength is altered, said alteration being measured with the aid of any usual wavelength measurement technique.

Thus, the invention provides a pH sensor where a transducer mechanically couples an optical fiber containing a Bragg grating to a pH-sensitive hydrogel.

The invention also provides a pH sensor where the hydrodynamic volume change of the pH-sensitive hydrogel causes a change of the strain to which the FBG is submitted, which can be evaluated through the change of the Bragg wavelength.

The invention provides still a pH sensor to be placed in a well, in pipes and difficult access equipment to measure pH together with other FBG sensors used to measure parameters such as downhole pressure, temperature and flow rate.

The invention additionally provides a pH sensor to be placed in a well, in pipes and difficult access equipment, the obtained pH measurements allowing the indirect evaluation of the corrosion rate.

The invention provides further a pH sensor where the set of polymer discs contains different hydrogels that are sensitive to different pH ranges, so as to sweep a wide range of pH values.

The invention provides also a pH sensor that can be placed in series with at least one more sensor containing a hydrogel that is sensible to a different pH range while utilizing the same optical fiber.

BRIEF DESCRIPTION OF THE DRAWINGS

FIG. 1 attached illustrates the change in hydrodynamic volume of a pH-sensitive hydrogel with a change in the pH of the medium.

FIG. 1A schematically illustrates a hydrogel. FIG. 1B illustrates the situation where the hydrogel is immersed in a medium with high pH, while FIG. 1C illustrates a hydrogel in a low pH medium.

FIG. 4 attached illustrates a section of the same mode of the inventive pH sensor using a spring. FIG. 4A illustrates the body of the pH sensor while

FIG. 9 attached illustrates another mode of the pH sensor where the transducer is a beam. FIG. 9A is a schematic drawing of the sensor using a beam while

DETAILED DESCRIPTION OF THE PREFERRED MODES

Figure 2:
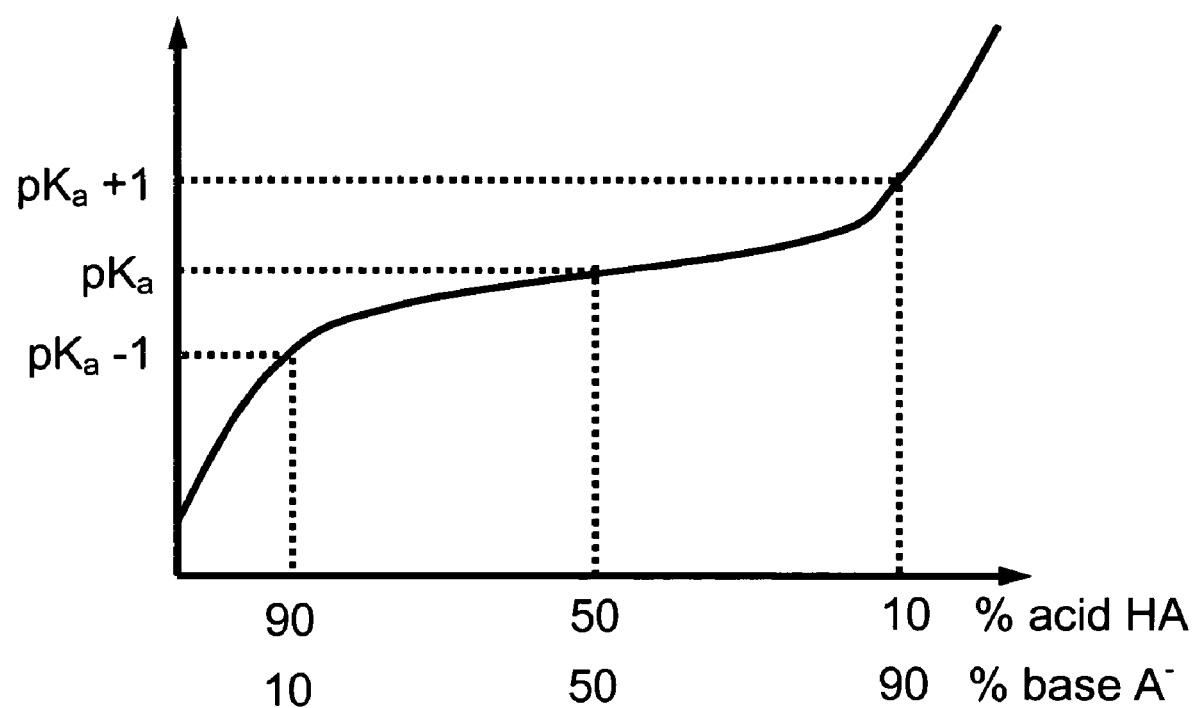
FIG. 2 attached is a graph of the titration curve of a weak acid with a strong base, so as to show the buffering effect.

As previously described, the optical fiber pH sensor of the invention for the measurement of pH utilizes a transducer that mechanically couples an optical fiber containing a Bragg grating, to a pH-sensitive hydrogel.

The concept of the present invention is therefore based on the fact that the mechanical features as well as the pH sensitivity of a hydrogel combined to a mechanical device making compatible the stress-strain properties of the said device with those of an optical fiber containing a Bragg grating allows recovering the information of the pH value of an aqueous solution to the optical domain, yielding a fiber Bragg grating pH sensor.

For the purposes of the invention, a useful hydrogel is any hydrogel sensitive to the pH range that one desires to measure. Thus, the inventive sensor is not limited to a specific hydrogel, on the contrary, it contemplates the use of several hydrogels, which can be sensitive to wide pH ranges since around 2.0 and up to around 12.0. Thus, it will be apparent to the experts that although the specification is more specifically directed to a hydrogel based on the PVA/PAA polymer, which is sensitive to pH in the range between 2.5 and 7.0, more specifically in the range from 3.0 to 6.0, this being the range of interest for the present study, said choice does not mean a restriction of the invention, being only an example of it.

Within the PVA/PAA polymer chains in aqueous medium, the change of hydrodynamic volume due to pH changes is governed by three parameters: the restoring force provided by the polymer chain, the chemical affinity between the solid and fluidic parts of the hydrogel, and mobility of the hydrogen ion. The combination of these parameters can be described by the osmotic pressure, which arises when there are equilibrium changes, and leads to changes of the hydrodynamic volume. The restoring force, which is provided by the crosslinks and whose magnitude only depends on temperature, acts as to maintain the hydrogel volume in an equilibrium state. Chemical affinity is responsible for the attraction or repulsion between polymer chain and solvent, accomplished by the presence of electric charges; it does not depend on temperature, but is affected by the polymer hydrodynamic volume and by the solvent. The mobility of the hydrogen ion depends on the degree of ionization of the polymer chain, on the temperature, on the degree of crosslinking of the chain and on the hydrodynamic volume.

The invention will now be described based on the attached Figures.

The volume change in a hydrogel such as the PVA/PAA hydrogel represented in FIG. 1 is interpreted on the basis of the chemical affinity between carboxyl group and water molecules, and of the restoring force provided by the crosslinks. On the other hand, the dynamics of such change is interpreted on the basis of the hydrogen ion mobility within the polymer chain.

Therefore, in a less acidic medium (pH>5) the $H^+$ ions concentration is reduced, with a shift of the reaction equilibrium $[-COOH]_n \rightleftharpoons [-COO^-]_n$ towards the formation of acetate groups $([-COO^-]_n)$ that yield negative charges in the polymer chain, those meaning repulsion, that is, increased volume.

In an acidic medium (pH<4) the increase in the $H^+$ ion concentration shifts the reaction equilibrium $[-COO^-]_n \rightleftharpoons [-COOH]_n$ towards the formation of acidic groups $([-COOH]_n)$, which reduce the negative charges in the polymer chains, neutralizing said charges and causing volume reduction.

Since the involved reactions are reversible, the pH change only alters the balance point of the reaction and, in this way, the hydrodynamic volume. The rate at which the volume change occurs depends on the hydrogen ions mobility.

PVA (poly vinyl alcohol) and PAA (polyacrylic acid) polymers are commercial products supplied by Aldrich, USA.

The preparation of the PVA/PAA polymer comprises state-of-the-art procedures adapted to the hydrogel used in the inventive pH sensor.

Said procedure comprises the steps of polymer solution preparation, drying of the solution to obtain a film and thermal crosslinking of the obtained film to yield the PVA/PAA hydrogel.

The procedure comprises therefore the following steps:
a) Prepare a 3.0% by weight solution of PAA with viscometric average molecular weight Mv=1,250,000 and a 3.0% by weight solution of PVA 89%-hydrolyzed in water with weight average molecular weight Mw=31,000–50,000, by slowly adding 3.0 g of polymer in 100 mL water at 50° C. under continuous agitation (during 2 hours);
b) After cooling the solutions to room temperature, add water to compensate for evaporation;
c) Obtain a PVA/PAA mixture at a ratio of 1.5% by mixing the PVA and PAA solutions at a proportion of 1:1 during 5 hours at 50° C. under agitation;
d) Pipette 50 mL of the 1.5% PVA/PAA mixture on a flat glass plate;
e) Dry the mixture in an oven at 55° C. during 24 hours, to obtain a polymeric film 0.10 mm to 0.30 mm thick;
f) Recover the obtained film and cut it into slices, placing them in an oven at 100° C. during 1 hour to form crosslinks between the two polymers;
g) Provide 270 g weights and clamps to stretch the slices during 20 minutes at 100° C., to stabilize the crosslinks;
h) Recover the crosslinked PVA/PAA polymer slices and remove the weight and clamps after cooling.

The pH value provided by the sensor is related to the $pK_d$ (logarithm of the reciprocal of the dissociation constant) of the weak acid or weak base contained in the polymer chain.

It is well known that in aqueous solutions almost all the strong acid molecules are dissociated into ions. On the other hand, weak acids do not completely dissociate. Thus, for these latter it is possible to calculate a constant able to relate the amount of dissociated molecules and the amount of non-dissociated molecules when the system reaches equilibrium.

Such equilibrium constant is called dissociation constant ($K_d$), which is ($K_a$) for acids. For strong acids, this kind of relationship is meaningless in view of the fact that the number of non-dissociated molecules is neglectable.

The equation suggested by Arrhenius for the dissociation of an acid HA is:

$$HA_{(aq)} \rightleftharpoons H^+_{(aq)} + A^-_{(aq)}$$

On the other hand, the equation proposed by Brönsted-Lowry stresses the fact that the acid transfers a proton to water:

$$HA_{(aq)} + H_2O_{(l)} \rightleftharpoons H_3O^+_{(aq)} + A^-_{(aq)}$$

The condition for such equilibrium is written as $[H_3O^+][A^-]/[HA][H_2O]$.

However, since the concentration of water molecules remain constant (of the order of 55.5M, $[H_2O]=1000$ g/L/ 18.015 g/mol=55.5M), that is, does not influence the calculations of equation $HA \rightleftharpoons H^+ + A^-$, the equilibrium can then be written as $[H^+][A^-]/[HA]$. This would be the same as considering the $H_3O^+$ ion just as $H^+$, but since there is no free proton, one should be aware that $H^+$ is presented as $H_3O^+$.

Therefore the dissociation constant ($K_a$) for a weak acid HA can be defined as:

$$K_a = [H^+][A^-]/[HA]$$

Rearranging and applying the logarithm in the Henderson-Hasselbach equation that relates pH with $pK_a$ of a given solution:

$$pH = pK_a + \log[A^-]/[HA]$$

Replacing figures in the equation, and drawing a titration curve as in FIG. 2, it can be seen that the buffering effect of the solution is limited to a range of pH values between $pK_a+1$ and $pK_a-1$. Out of this range, a small addition of acid or base leads to a huge pH change.

The strength of an acid, that is, its ionization degree in solution is indicated by the magnitude of its dissociation constant ($K_a$). The weaker the acid, the lower the $K_a$ value. For polyprotic acids, that is, acids that bear more than one ionizable hydrogen, there will be more than one dissociation constant. This is because the ionization of a polyprotic acid occurs by steps, and each step will show an associated $K_a$ value.

Aiming to assess the predominant working range of the PVA/PAA polymer hydrogel, its $pK_a$ was determined by titrating 1 g of a previously hydrated polymer film sample, the titration being carried out with a 0.13M NaOH solution.

Based on the titration results, a $pK_a=4.6$ was obtained for the sample, which is a coherent figure for a weak acid.

Experimental results show that the sensitivity of the inventive pH sensor should not be affected by the buffering effect of the polymer film since, considering that the medium is infinite the polymer film should always attain such pH value, only the response time of the sensor being affected.

Depending on the number of pH-sensitive discs or on the uncertainty of the Bragg wavelength measurement, experimental results further show that the range of pH reading varies from ($pK_a-2$)–($pK_a-3$) up to ($pK_a+2$)–($pK_a+3$).

In an analogous way as performed for the PVA/PAA polymer hydrogel used in the here proposed sensor, other polymer-based hydrogels and/or different polymers can be submitted to the same kind of titration described herein before, so as to determine the pH ranges at which said hydrogels are sensitive.

Thus, it is clear that the inventive sensor in its several modes is not limited to the PVA/PAA polymer hydrogel, such hydrogel being only a non-limiting example of the invention.

The Bragg gratings on their turn consist in a local, longitudinal, periodic modulation of the optical fiber core refractive index. The grating works as an optical spectral filter, reflecting light with a narrow bandwidth around the Bragg wavelength $\lambda_B$, which corresponds to approximately three times the value of the spatial period $\Lambda$ of index modulation, according to $\lambda_B = 2n\Lambda$, with $n \approx 1.5$ being the refractive index of the optical fiber core.

Bragg gratings useful for the purposes of the invention comprise the gratings prepared previously to the pH sensor installation. For this purpose, the optical fiber core is locally exposed to an interference pattern of two ultraviolet light beams so oriented relative to the optical fiber longitudinal axis that, for the grating, the maxima and minima of the interference pattern extend along a small portion of the optical fiber in directions normal to the longitudinal axis and that the periodicity is that desired for the particular grating.

The experiments conducted by the Applicant aiming to the development of the present pH sensor have shown that the volume change of the PVA/PAA hydrogel in the acid range between 2.5 to 7.0, more specifically 3.0 to 6.0 pH units, is sufficient to impart a strain in a Bragg grating so that its wavelength is altered by hundreds of picometers. The uncertainty of the adopted wavelength measurement system is ±1 pm.

The resolution of the inventive pH sensor varies between 0.1 up to 0.05 pH units.

The sensor is comprised by a standard monomode optical fiber containing the FBG in the fiber core at any position along the fiber. The FBG mechanically coupled to the transducer is interrogated using an optical system made up of a light source—that can be a wavelength tunable laser or a broadband source of light, such as a LED (light emitting diode) or an ASE (amplified spontaneous emission) source—coupled to the fiber core, and a system for the measurement of the Bragg wavelength—that can consist of a spectrum analyzer or by a system containing spectral filters of any kind and a photodetector for measuring the convolution of the signal from the FBG with that of the filter.

After illuminating the FBG, light can be detected in transmission or in reflection. In case the detection is carried out in transmission, one must be concerned with the wavelength at which the loss of optical power is maximum. In case the reflected signal is detected, one must retrieve the maximum optical power and measure the wavelength at that point. In this case, a 50%—50% fiber coupler is generally used, through which the light from the source is sent to the sensor and the spectrum reflected by the FBG is sent to the measurement system. For downhole applications or in any circumstances that present access difficulty, measurements should be carried out in reflection. From the measurement of the Bragg wavelength, it is possible to retrieve the desired mensurand value by means of a calibration curve prepared prior to installing the sensor in the field.

Figure 3:
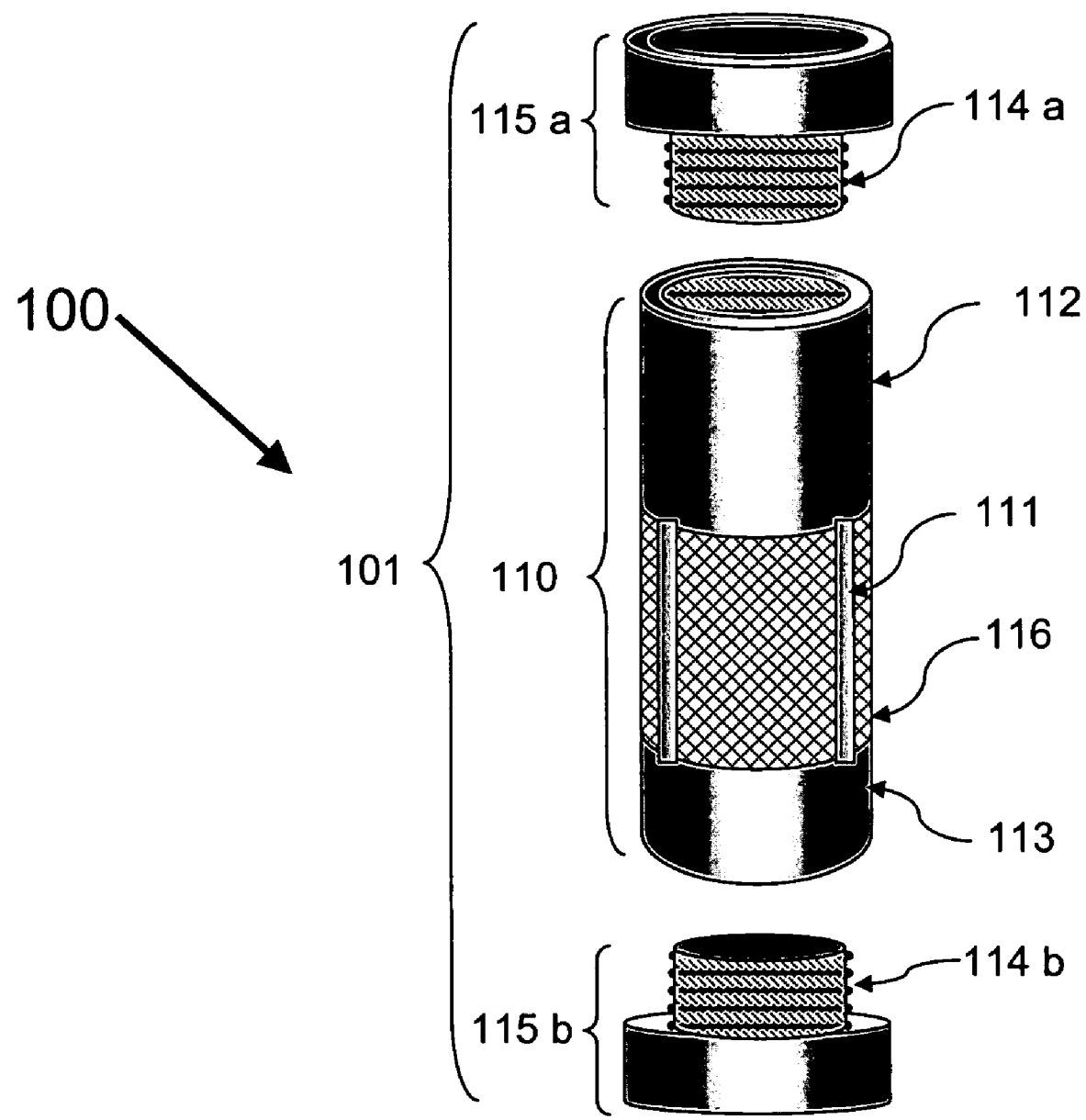
FIG. 3 attached schematically illustrates one mode of the pH sensor of the invention, said mode utilizing a spring as mechanical transducer between the hydrogel and the optical fiber containing a Bragg grating.

FIG. 3 is a general view of one mode of the invention where the mechanical transducer is a spring. This Figure shows a view of the pH sensor, generally designed by numeral 100, having an external body 101, usually built in Teflon and generally cylindrical, the central portion of it being designed by 110. The machining of the central portion 110 of the body 101 is performed to make easier the expansion of the hydrodynamic volume of polymer discs 125. Thus, the central portion 110 of the body 101 is bored, parts 112 and 113 being connected by at least three rods or bars 111. Part 112 is fitted with inner threads (not represented) machined to be adapted to the outer threads 114a of cover 115a of sensor 100.

In analogy to the description of part 112, a cover 115b provided with outer threads 114b is adapted to the inner (not represented) threads of part 113 of central part 110 of sensor 100. A steel screen 116 serves as a lateral support for the polymer discs (not represented) contained in the interior of sensor 100. The central part 110 contains an optical fiber with a Bragg grating, a spring and optical fiber fixation discs, polymer discs and spacers (not represented).

Figure 4A:
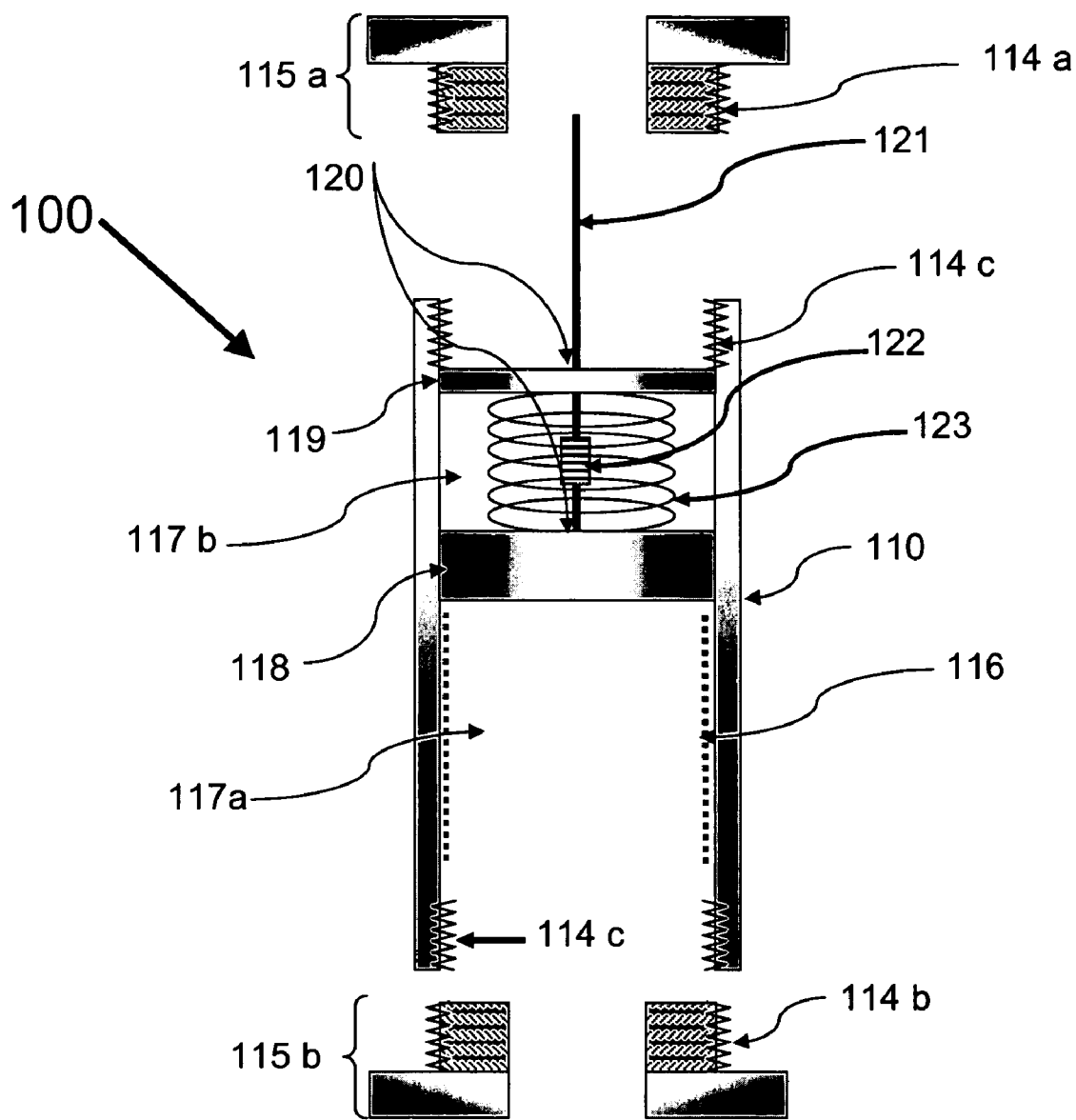
Figure 4B:
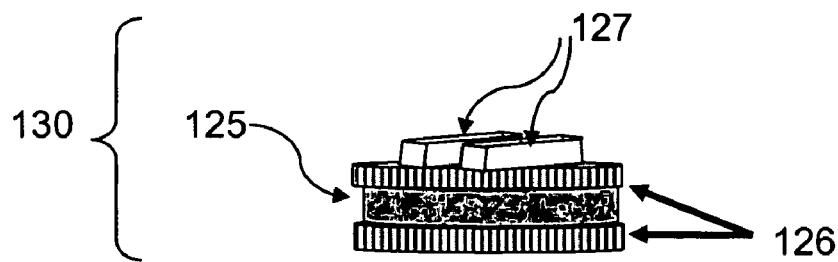
FIG. 4B illustrates in detail the polymer disc and steel screens.

FIG. 4A illustrates a section of the pH sensor 100. In central part 110 of sensor 100 are placed the optical fiber 121 with the Bragg grating 122, the spring 123, a movable disc (piston) 118 and a fixed disc 119 for attaching the fiber 121 and a screen cylinder 116. Also placed in said central part are hydrogel discs 125 having widths between 0.10 mm and 0.30 mm prepared as described hereinbefore, discs 126 made up of steel screens 100 mesh Tyler (0.149 mm) for the confinement of hydrogel discs 125, and spacers 127 as illustrated in FIG. 4B, those making up the disc units 130.

Spacers 127 and steel screen discs 126 are used to separate hydrogel discs 125 aiming to improve the contact area of hydrogel discs 125 with the solution whose pH is to be monitored, and consequently, to reducing the response time of sensor 100.

In FIG. 4A are also indicated the inner threads 114c that are adapted to outer threads 114b of cover 115b of sensor 100.

Disc units 130 are housed in a first compartment 117a of the body 110 of sensor 100. Compartment 117a is limited by a piston 118 and by cover 115b. Piston 118 and disc 119 for attaching the optical fiber mark the limits of a second compartment 117b of the central part 110 of sensor 100. In a less acidic medium, the PVA/PAA hydrogel swells and presses the piston 118, and therefore the spring 123, giving rise to a reduction of the strain to which the optical fiber 121 containing the Bragg grating 122 was originally submitted.

The number of hydrogel discs 125 is not critical and can vary from a minimum of two up to a number such that the volume change of said discs 125 does not affect the fiber 121 integrity. The minimum number of discs 125 for the sensor 100 is that required to lead to a Bragg wavelength change of at least 60 pm, so as to assure the performance of a pH measurement in the range of interest (between 3.0 and 6.0 for petroleum wells) with resolution of 0.05 pH units. However, if a wider range and/or a higher pH resolution are desired, said minimum amount of discs 125 can be increased.

FIG. 4B illustrates a disc unit 130 to be inserted in sensor 100, said unit being made up of the hydrogel disc 125 itself, steel screen discs 126 and spacers 127.

Optical fiber 121 is introduced in central part 110 through bores 120 performed in fixed disc 119 and in piston 118, the optical fiber being attached to these two sites using any known technique, such as for example with the aid of an adhesive or by using a metal ring.

Spring 123 assures the strain of the optical fiber 121 and therefore, of the Bragg grating 122.

The elasticity constant of spring 123 is between 50 N/m and 200 N/m.

To attach fiber 121, spring 123 is partially compressed, so as to keep the FBG 122 deformed. After attachment, cover 115a is fitted and threaded in central part 110 with the aid of threads 114a and adjusted so that the fiber 121 is strained by spring 123.

The setting up of sensor 100 is carried out according to the following steps:

a) Threading cover 115b in central part 110;
b) Providing disc units 130 and introducing same in compartment 117a;
c) Providing an optical fiber 121 containing a Bragg grating 122, and passing said fiber 121 through bore 120 so as to attach fiber 121 on piston 118;
d) Introducing said optical fiber 121 attached on piston 118 in central part 110 and positioned on the disc units 130;
e) Positioning spring 123 on piston 118 by passing fiber 121 through said spring 123;
f) Passing fiber 121 through bore 120 of disc 119;
g) Threading cover 115a in central part 110 so as to compress spring 123;
h) Attaching fiber 121 on disc 119;
i) De-threading cover 115a so as to impart a strain on fiber 121 and alter the wavelength $\lambda_B$ of FBG 122 of a value between 100 pm and 5 nm; and
j) Obtaining sensor 100 set and ready for use.

So-mounted pH sensor 100 is then placed in an aqueous solution at pH 3.0 for the polymer initial hydration, this leading to an expansion of the hydrodynamic volume caused by the entering solution in the polymer chain. Such expansion causes a force that compresses string 123, resulting into a reduction of the strain to which the optical fiber 121 was originally submitted. The pH sensor 100 is thus ready for use.

Figure 5:
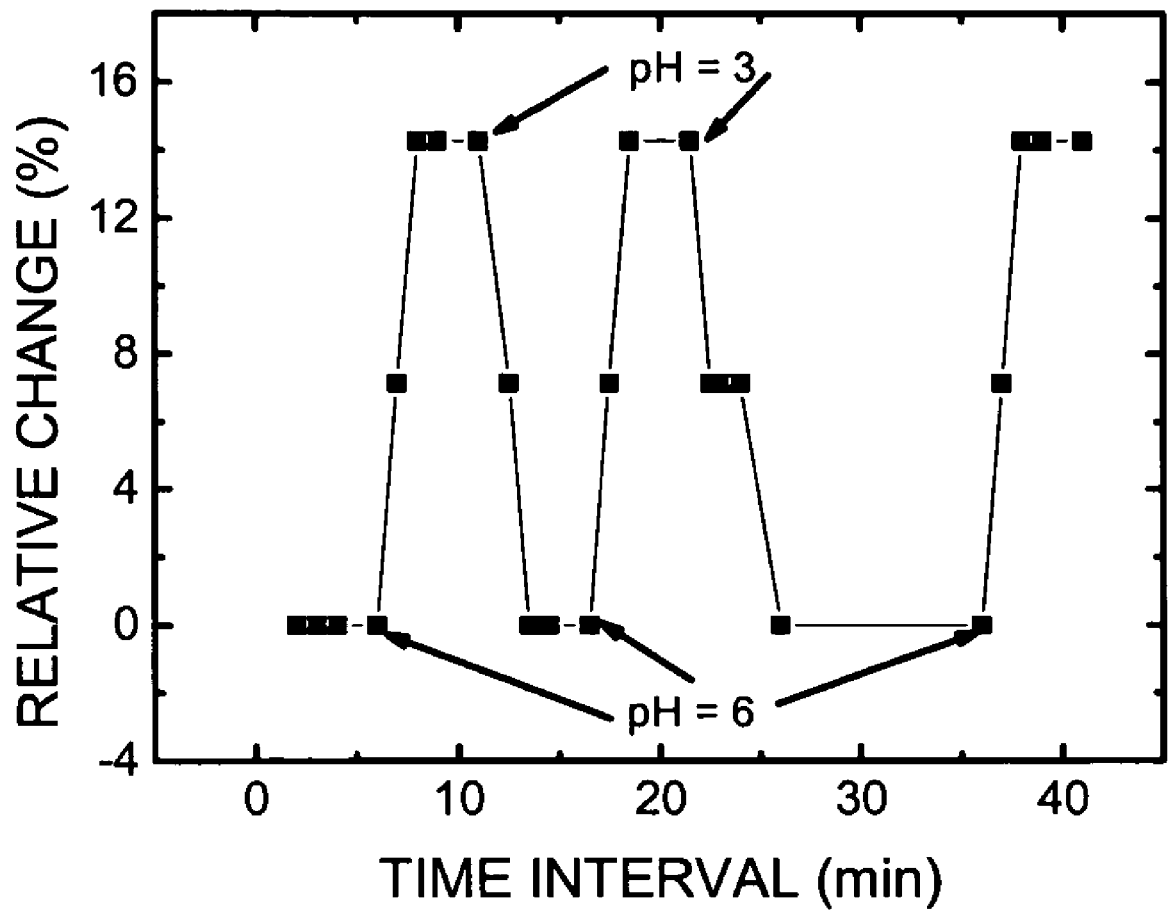
FIG. 5 attached illustrates the relative change of the lateral dimensions of a free PVA/PAA hydrogel sample at pH 4.0, 5.0, and 6.0 as compared to the value of said dimensions at pH 3.0.

FIG. 5 illustrates the expansion of the hydrodynamic volume of free PVA/PAA hydrogel discs 125 at pH 6.0 as related to the value of said volume at pH 3.0. The graph illustrated in said FIG. 5 shows a relative change of 14% of the hydrogel hydrodynamic volume, the response time being of a few minutes.

Figure 6:
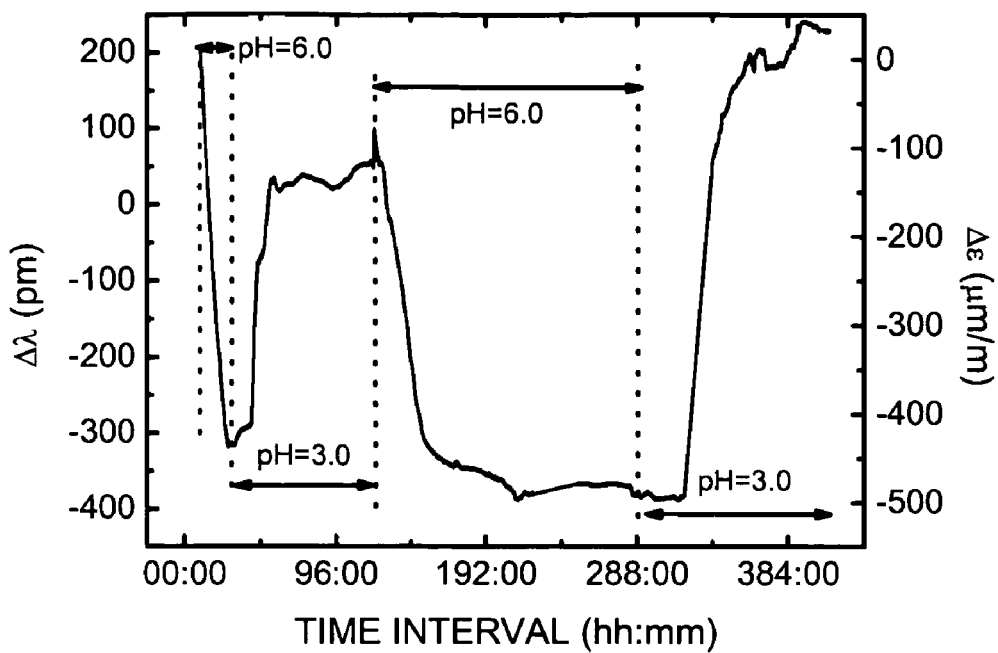
FIG. 6 attached illustrates the experimental result obtained with the sensor embedded in buffer solutions with pH 3.0 and 6.0.

FIG. 6 illustrates the experimental data of the Bragg grating wavelength change when pH sensor 100, with the previously hydrated polymer discs 125 in a pH 3.0 buffer solution is initially immersed in a pH 6.0 buffer solution, and then immersed in a pH 3.0 buffer solution and thus successively.

As result of the first immersion of the sensor in a pH 6.0 buffer solution, a Bragg wavelength change by 545 pm is observed, this being equivalent to a fiber strain variation of approximately 450 μm/m. In the sequence, by changing to a pH 3.0 solution, a 370 pm change is observed for the Bragg wavelength, that is, a 305 μm/m change in the fiber strain. Further cycles show equivalent changes in the strain transmitted to the optical fiber. Also, the figures for the force exerted by the polymer discs on the spring during the various pH 3.0 and 6.0 cycles are similar, varying from 0.27 N to 0.47 N.

Figure 7:
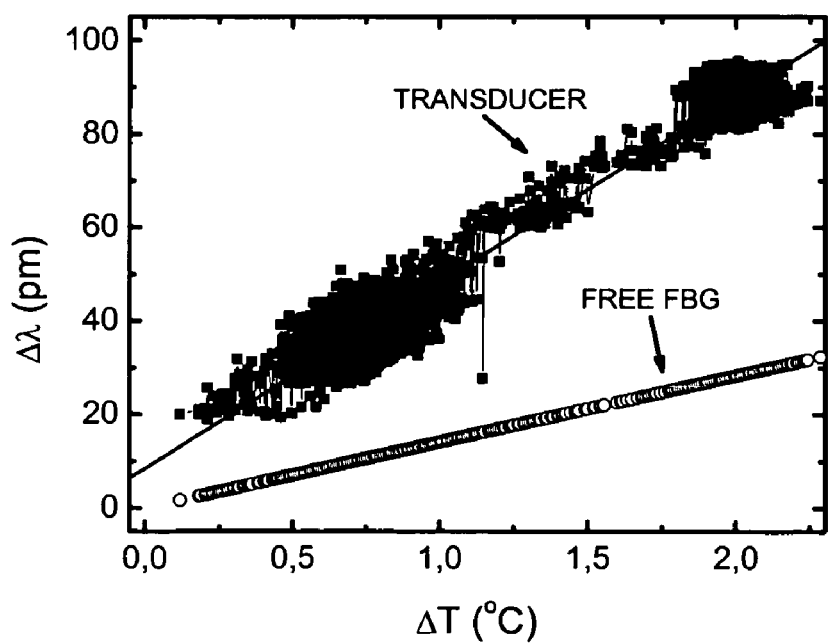
FIG. 7 attached is a graph showing the sensor response to temperature changes, as compared to the response of a free Bragg grating.

The small oscillations of the wavelength values during the pH cycles are due to small variations of the solution temperature during the test, those influencing not only the signal from the Bragg grating but also the thermal expansions of the sensor body, this having been duly quantified, as shown in FIG. 7.

Figure 8:
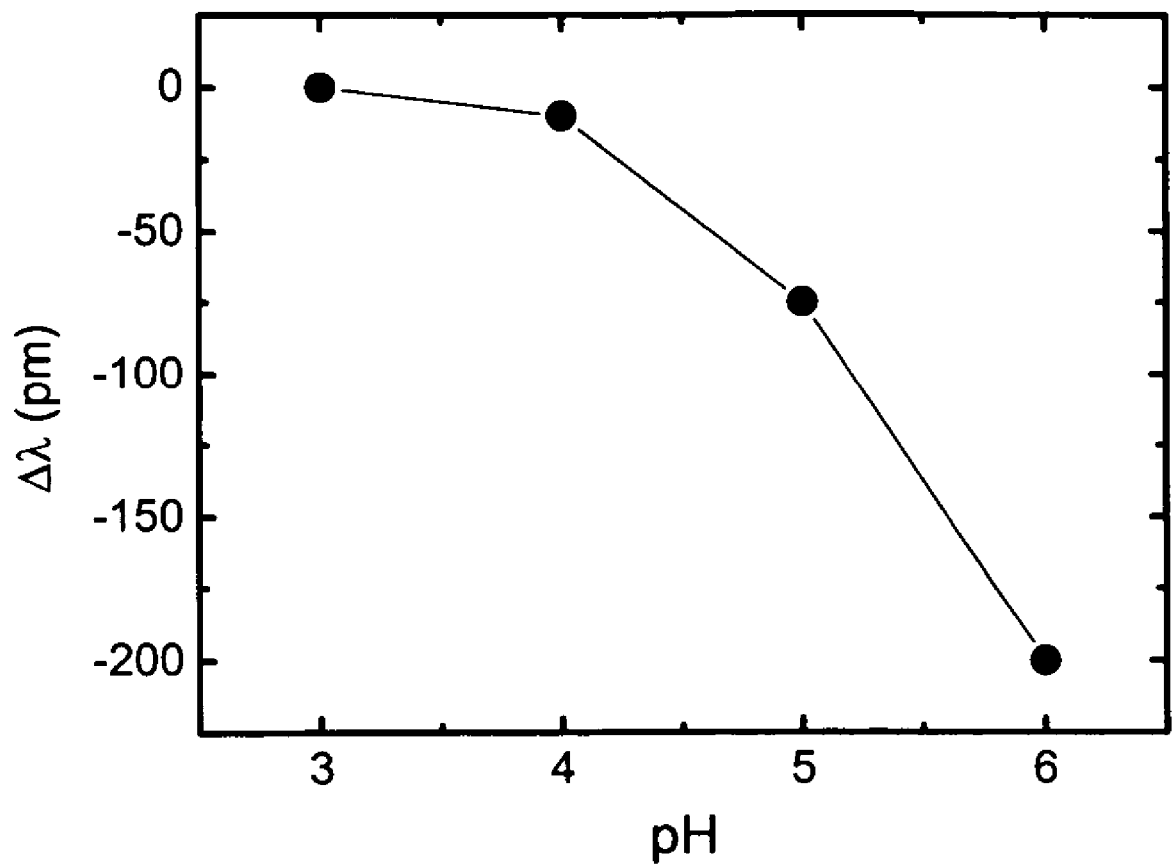
FIG. 8 attached is a graph showing the change of the Bragg wavelength in the sensor for several pH values of the buffer solution where said sensor is immersed.

A graph illustrating the grating wavelength change in sensor 100 as a function of the pH of the buffer solution where the sensor 100 is immersed can be seen in FIG. 8.

An important parameter securing the industrial applicability of pH sensor 100 is the response time. It was found that this time is around 24 hours for an available polymer hydration surface of 18%, this being suitable for the final intended use. The main factor affecting this parameter is the exposed surface to the medium, enabling higher proton and water molecules mobility and therefore a quick change of the hydrodynamic volume.

Since the response time of sensor 100 is directly linked to the hydration rate of the polymer discs, the effective hydration surface area of the hydrogel discs 125 could be estimated.

For this purpose, the hydrogel discs 125 surface area is calculated, as well as the surface occupied by spacers 127, the open surface of screen 116 and that of steel screen discs 126. Calculations lead to percentages of up to 42.6% of hydrogel surface available for hydration as the screen mesh becomes more open (between 0.149 mm and 0.297 mm).

For larger hydration surfaces the response time is reduced, this being an interesting operation feature, in spite of the fact that it is not possible to excessively increase the surfaces in view of the risk of having an unsuitable spatial hydrogel confinement.

Also, experiments conducted at temperatures between 22.0° C. and 70.0° C. have shown that, if a volume change of the free hydrogel with temperature is observed, such change is lower than 5%, at pH 3.0 as well as at pH 6.0.

A variant of the mode of sensor 100 using a string is one where central part 110 is opened into two troughs (not represented), this making easier the setting of the fiber 121/spring 123 system, as well as the accommodation of hydrogel discs 125 with contention screen 116.

Another mode of the pH sensor using the concept of the invention is a pH sensor generally designed by numeral 200 having an outer body 201 containing a central part 210 having a bored area and supporting rods or bars 111, where spring 123 is replaced by a thin metal beam 215, actuated by a piston 214 positioned on hydrogel discs 125 as illustrated in FIGS. 9A, 9B, 10A and 10B.

Figure 10A:
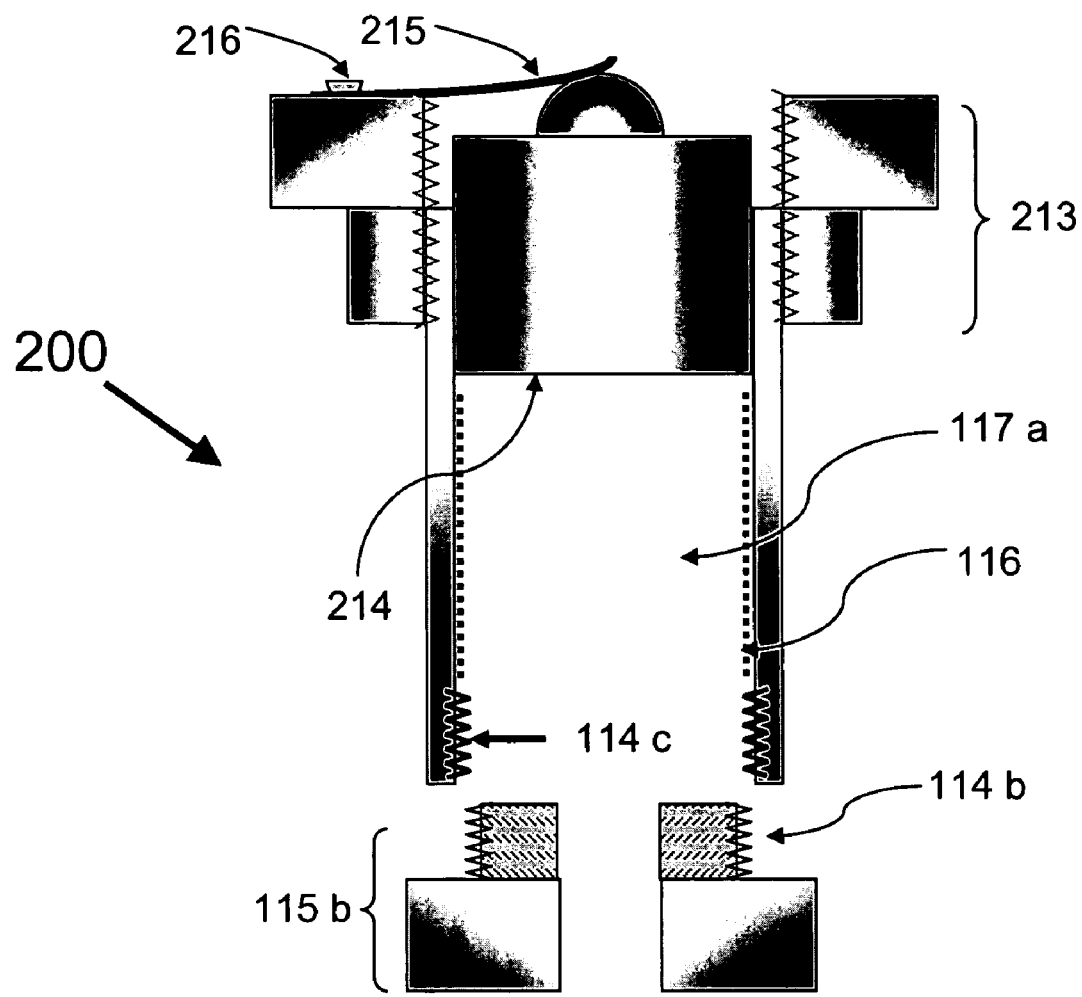
FIG. 10A attached schematically illustrates a normal cross-section of the sensor utilizing a beam while FIG. 10B attached illustrates the fixation of the beam on the sensor cover.
Figure 10B:
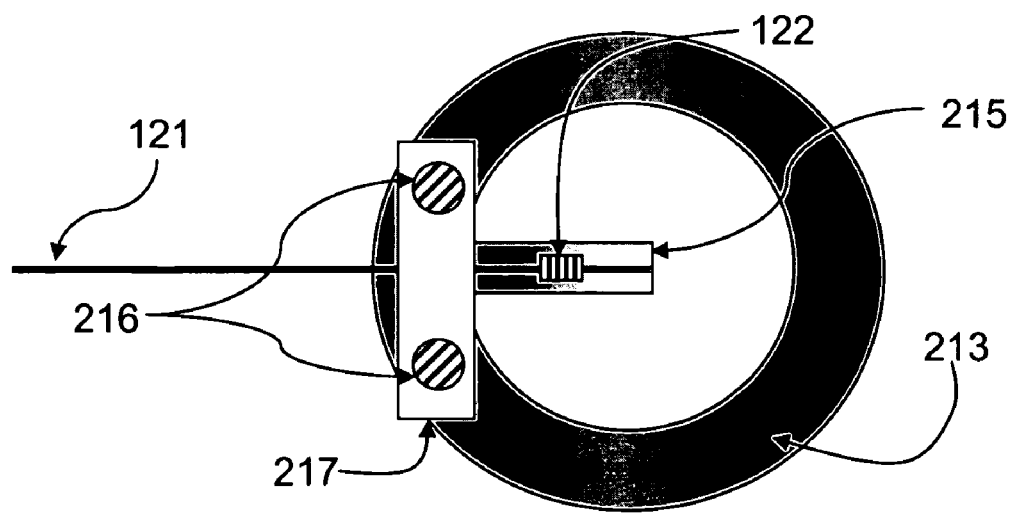

As can be seen in FIGS. 10A and 10B, beam 215 is attached to sensor 200 cover 213 through, for example, a fixation plate 217 and screws 216.

Figure 9A:
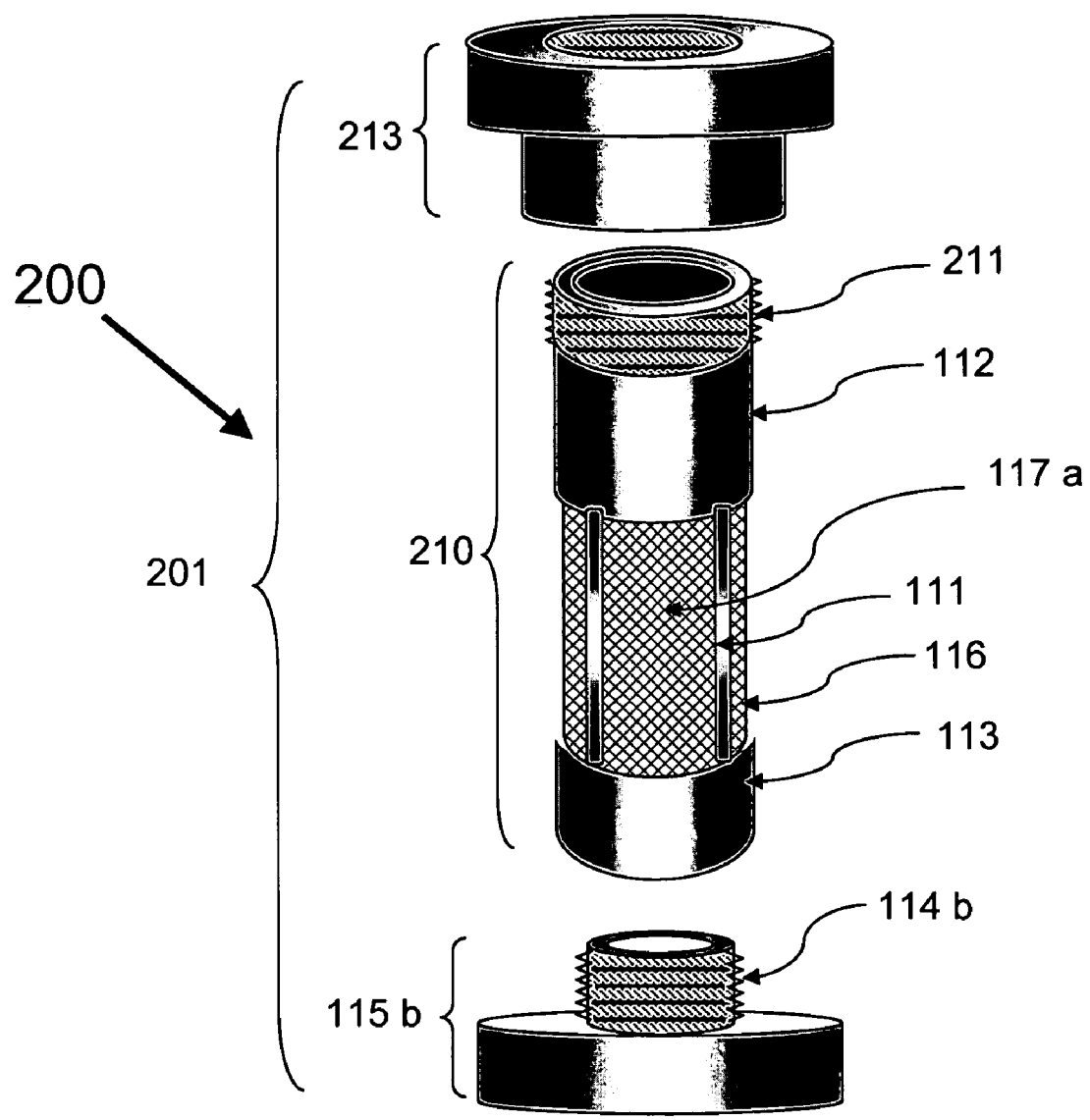
Figure 9B:
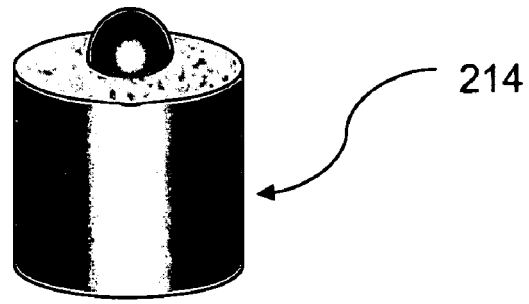
FIG. 9B illustrates the piston actuating on the beam.

According to FIGS. 9A and 10A, it can be seen that other features of sensor 200 are similar to those of sensor 100 as regards construction and housing of disc units 130.

An optical fiber 121 containing a Bragg grating 122 is so positioned that grating 122 is placed at the center of beam 215, as indicated in FIG. 10B, and the displacement of beam 215 due to the hydrogel hydrodynamic volume change will cause a strain in grating 122, said strain being then measured.

Sensor 200 and the dimensions of beam 215 are calculated taking into consideration the magnitude of the force exerted by the polymer system of discs 125 as well as the desired amount of grating strain, as described below.

Young Modulus of the optical fiber: $E_f = 7.3 \times 10^{10} \ N/m^2$

Young Modulus of steel: $E_{steel} = 210 \times 10^9 \ N/m^2$

Fiber radius: $r_f = 62.5 \times 10^{-6} \ m \Rightarrow$ Fiber surface: $S^f = 12.27 \times 10^{-9} \ m^2$ Copolymer disc 125 radius: $r_p = 7.5 \ mm \Rightarrow$ Polymer surface: $S_p = 176.71 \times 10^{-6} \ m^2$ If one considers a grating wavelength change of nearly 120 pm upon going from a pH=3.0 solution to a pH=6.0 solution, the following data are obtained:

Strain undergone by the fiber: $\epsilon \sim 100 \ \mu\epsilon$

Stress on the fiber:

$$\sigma_f = E_f \times \epsilon = 7.3 \times 10^6 \ N/m^2$$

For sensor 200 the force exerted by hydrogel discs is also calculated:

Hydrogel force on the fiber:

$$F_p = \sigma_f \times S_f = 7.3 \times 10^6 \ N/m^2 \times 12.27 \times 10^{-9} \ m^2 = 0.089 \ N$$

For a beam having the following dimensions:
Length: l=21.5 mm
Width: b=3 mm
Height: h=0.1 mm The expected stress $\sigma_{beam}$ and the strain $\epsilon_{beam}$ of beam 215 at the point of maximum strain (embedment point) is calculated.

Neutral line: $r = h/2$ $$\sigma_{beam} = (M \times r)/I$$

$$I = (b \times h^3)/12$$

$$M = F \times l$$

$$\sigma_{beam} = (6 \times F_p \times l)/(b \times h^2) = 3.83 \times 10^8 \ N/m^2$$

$$\epsilon_{beam} = \sigma/E_{steel} = 3.83 \times 10^8 \ N/m^2 / 210 \times 10^9 \ Pa = 1822 \ \mu\epsilon$$

as well as in the center of beam 215:

$$l/2 = 10.75 \ mm$$

$$\sigma_{beam} = (3 \times F_p \times l)/(b \times h^2) = 1.92 \times 10^8 \ N/m^2$$

$$\epsilon_{beam} = \sigma_{beam}/E_{steel} = 911 \ \mu\epsilon$$

The calculations shown above demonstrate that for a fiber 121 containing a Bragg grating attached to the center of beam 215, there will be a change of the Bragg grating by approximately 1 nm, this being widely sufficient for the purposes of the sensor developed by the Applicant.

Still another mode of the invention relates to a pH sensor generally designed by numeral 300, where the optical fiber 121 containing the Bragg grating 122 works as a mechanical transducer (not represented).

Figure 11:
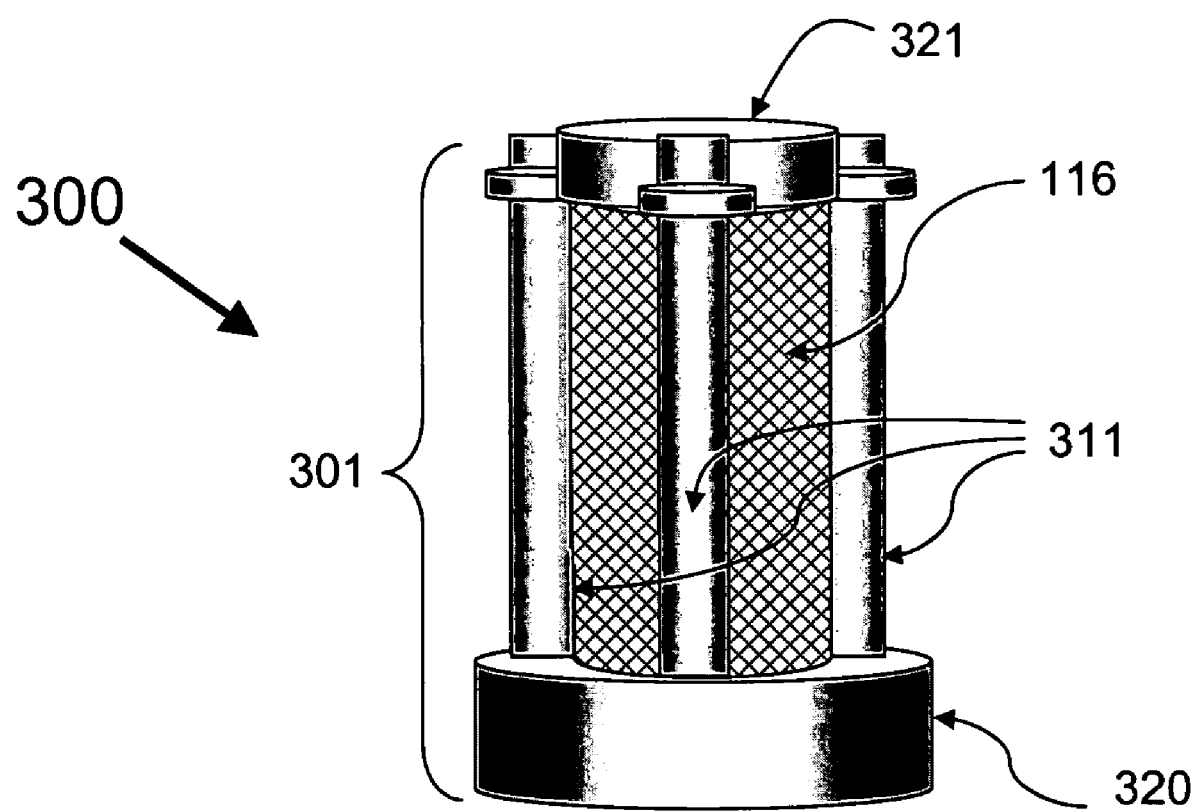
FIG. 11 attached illustrates a general view of another mode of the inventive pH sensor using the optical fiber as transducer.

FIG. 11 shows an outer view of sensor 300 with a body 301 containing guides or bars 311 and a base 320 as well as a movable disc 321 working as a piston.

Figure 12:
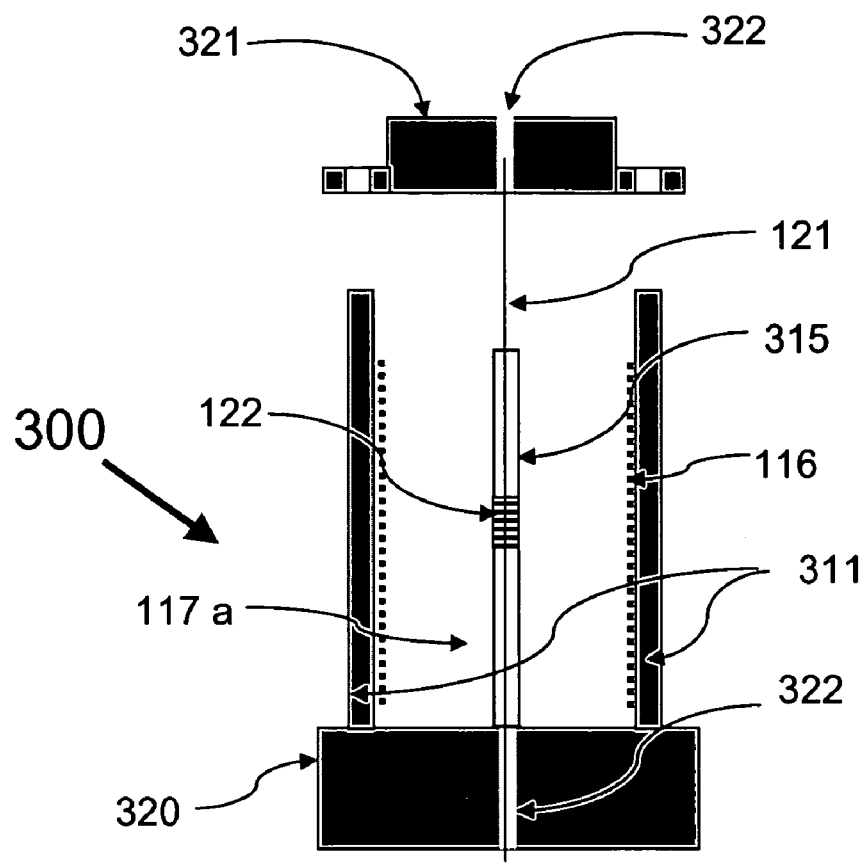
FIG. 12 attached illustrates a section of the inventive pH sensor using the optical fiber as transducer.

FIG. 12 shows a cross-section of pH sensor 300. The optical fiber (not represented) is introduced through bores 322 and attached using any known devices to two steel discs 320,321. The disc having numeral 320 makes up one of the ends or base of sensor 300 and is integral with body 301 of sensor 300, and disc 321 makes up the other end of sensor 300 and can move by the action of hydrogel discs 125. The movement of movable disc 321 fitted with bores 323 is guided along three guides or bars 311 integral with body 301 of sensor 300. In order to minimize friction during the movement along the guides 311, disc 321 has generally a Teflon coating in the area internal to bores 323 that contact guides or bars 311.

Figure 13:
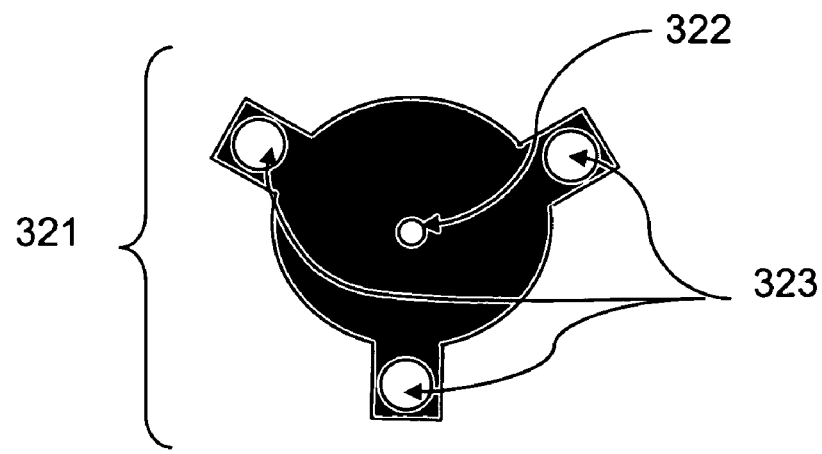
FIG. 13 attached illustrates the mobile disc of the sensor, which uses an optical fiber as transducer.

FIG. 13 illustrates an upper view of disc 321.

Optical fiber 121 is protected from possible shear forces using a small steel tube 315 through which the fiber is trespassed.

In an analogous way to the other modes of sensor 100, 200 in sensor 300 the hydrogel discs 125 are separated by steel screens 126 and steel spacers 127, forming the hydrogel discs units 130. In order to avoid friction of the steel spacers 127 with fiber 121 protecting tube 315, the contact area of same is covered with a slipping coat, generally of Teflon. A steel screen 116 cylinder laterally confines the hydrogel discs 125.

Alternatively, sensor 300 shows a configuration (not represented) similar to that of sensors 100, 200 described above, that is, an outer body 301 including separated compartments 117a, 117b respectively containing sets 130 of hydrogel disc units and the mechanical transducer (optical fiber 121).

The setting up of sensors 200,300 is analogous to that described for sensor 100, meeting the constructive modifications allowed to each mode.

In all the described modes of the inventive pH sensor 100, 200, 300 it is possible to pass fiber 121 containing a FBG 122 along the body of said sensor so that it is possible to connect same in series with other pH sensors and/or to sensors of other parameters of interest for the industry, such as pressure, temperature and flow rate.

As referred to above, the inventive sensor is not limited to the use of one single hydrogel being sensitive to a certain pH range. Thus, the invention encompasses sensor configurations or settings where discs of different hydrogels, sensitive to different pH ranges are packed successively in the same sensor body 110, 210, 301.

Still another variant is the one that comprises several sensors in series, each one containing a hydrogel sensitive to a certain pH range.

Still another variant is the one that comprises one single fiber containing more than one Bragg grating.

Still, the present sensor is able to work in series with downhole pressure, temperature and flow rate sensors, that is, it can be multiplexed with said other sensors.

Further, it should be obvious for the experts that the present sensor is useful not only for the pH measurement in petroleum well, but also in pipes and equipments that are hardly accessed, and also under ambient conditions.

The description and the considerations set forth in the present specification demonstrate the extreme versatility of the inventive sensor, since it is able to encompass a wide range of pH values of industrial interest, besides being able to be multiplexed to other optical fiber sensors in smart wells.

The invention claimed is:

1. An optical fiber pH sensor (100) for the measurement of the pH of aqueous solutions, wherein said sensor comprises:
   A) a generally cylindrical outer body (101) including:
   a) a central part (110), comprising:
   i) a first compartment (117a) containing a set of disc units (130) of a pH-sensitive hydrogel, said set being contained by a screen (116);
   ii) a second compartment (117b) containing a mechanical transducer (123) for transmitting strain to an optical fiber (121) containing a Bragg grating (122), the limits of said compartment being marked by a movable disc (118) between said first (117a) and second (117b) compartments and a disc (119) for attachment of an optical fiber (121);
   b) covers (115a) and (115b) at the ends of said outer body (101), and where:
   the change in pH of the tested solution causes a change in the hydrogel hydrodynamic volume, the strain caused by such volume change being transmitted to the Bragg grating (122) by the mechanical transducer (123) so as to alter the Bragg wavelength, said alteration being measured with the aid of usual techniques for wavelength measurement.

2. An optical fiber pH sensor (100) according to claim 1, wherein bores (120) through the central portions of disc (119) and of piston (118) make possible the passage and installation of the optical fiber (121) containing the Bragg grating (122) in compartment (117b).

3. An optical fiber pH sensor (100) according to claim 1, wherein the optical fiber (121) trespasses cover (115a) of body (101).

4. An optical fiber pH sensor (100) according to claim 1, wherein the setting up of said sensor comprises the following steps:
   k) threading cover (115b) in central part (110);
   l) providing disc units (130) and introducing same in compartment (117a);
   m) providing an optical fiber (121) containing a Bragg grating (122), and passing said fiber (121) through bore (120) so as to attach fiber (121) on piston (118);
   n) introducing said optical fiber (121) attached on piston (118) in central part (110) and positioned on the disc units (130);
   o) positioning spring (123) on piston (118) by passing fiber (121) through said spring (123);
   p) passing fiber (121) through bore (120) of disc (119);
   q) threading cover (115a) in central part (110) so as to compress spring (123);
   r) attaching fiber (121) on disc (119);
   s) de-threading cover (115a) so as to impart a strain on fiber (121) and alter the wavelength $\lambda_B$ of FBG (122) of a value between 100 pm and 5 nm; and
   a) obtaining sensor (100) set and ready for use.

5. An optical fiber pH sensor (200) for the measurement of the pH of aqueous solutions, wherein said sensor comprises:
   A) a generally cylindrical outer body (201), including:
   a) a central part (210), comprising a compartment (117a) containing a set of disc units (130) of a pH-sensitive hydrogel, said set being contained by a screen (116), and piston (214);
   b) a mechanical transducer (215) having attached thereto an optical fiber (121) containing a Bragg grating (122), said transducer (215) being attached to a cover (213) through fixation devices (216), (217);
   c) covers (115b) and (213) at the ends of the central part (210), and where
   the change in pH of the tested solution causes a change in the hydrogel hydrodynamic volume, the strain caused by such volume change being transmitted to the Bragg grating (122) by the mechanical transducer (215) so as to alter the Bragg wavelength, said alteration being measured with the aid of usual techniques for wavelength measurement.

6. An optical fiber pH sensor (300) for the measurement of the pH of aqueous solutions, wherein said sensor comprises:
   a generally cylindrical outer body (301) including:
   a) in one end, a disc (320) integral to said body (301) while another, movable disc (321) at the other end moves by the action of the set of hydrogel disc units (130) inserted in a compartment (117a) and contained in a screen (116), the movement of said disc (321) being guided along guides or rods (311) integral to said body (301);

b) an optical fiber (121) containing a Bragg grating (122), attached to discs (320), (321) and inserted in a protecting tube (315), and where the change in pH of the tested solution causes a change in the hydrogel hydrodynamic volume, the strain caused by such volume change being transmitted to the Bragg grating (122) by the optical fiber (121) so as to alter the Bragg wavelength, said alteration being measured with the aid of usual techniques for wavelength measurement.

7. An optical fiber pH sensor (300) according to claim 6, wherein the optical fiber (121) trespasses both discs (320), (321) of outer body (301).

8. An optical fiber pH sensor (100), (200), (300) according to claim 1, 5 or 6, wherein the sensor comprises at least two sets (130) of hydrogel discs.

9. An optical fiber pH sensor (100), (200), (300) according to claim 1, 5 or 6, wherein the sets of units (130) include hydrogel discs (125) separated by discs steel screens (126) and spacers (127).

10. An optical fiber pH sensor (100), (200), (300) according to claim 1, 5 or 6, wherein said hydrogel is pH-sensitive in the range around 2.0 up to around 12.0.

11. An optical fiber pH sensor (100), (200), (300) according to claim 10, wherein said hydrogel is pH-sensitive in the range between 2.5 and 7.0.

12. An optical fiber pH sensor (100), (200), (300) according to claim 11, wherein said hydrogel is a PVA/PAA polymer hydrogel.

13. An optical fiber pH sensor (100) according to claim 1, wherein the mechanical transducer (123) is a spring.

14. An optical fiber pH sensor (200) according to claim 5, wherein the mechanical transducer (215) is a beam.

15. An optical fiber pH sensor (300) according to claim 6, wherein the mechanical transducer is the optical fiber (121).

16. An optical fiber pH sensor (300) according to claim 6, wherein the optical fiber (121) trespasses discs (320), (321) to be connected to other sensors.

17. An optical fiber pH sensor (300) according to claim 16, wherein the other sensors are pH sensors.

18. An optical fiber pH sensor (300) according to claim 16, wherein the other sensors are pressure, temperature or flow rate sensors.

19. An optical fiber pH sensor (100), (200), (300) according to claim 1, 5 or 6, wherein the pH-sensitive hydrogel of discs (125) comprises only one kind of hydrogel and is sensitive to a certain pH range.

20. An optical fiber sensor (100), (200), (300) according to claim 1, 6 or 7, wherein the pH-sensitive hydrogel of discs (125) comprises two or more hydrogel kinds, sensitive to different pH ranges.

21. An optical fiber pH sensor (100), (200), (300) according to claim 1, 5 or 6, wherein it is linked in series, each sensor containing a hydrogel sensitive to a certain pH range, said sensors being connected to one single optical fiber.

22. An optical fiber pH sensor (100), (200), (300) according to claim 1, 5 or 6, wherein it is applied to smart wells together with other Bragg grating optical fiber sensors for the measurement of pressure, temperature and downhole flow rate.

23. An optical fiber pH sensor (100), (200), (300) according to claim 1, 5 or 6, wherein the sensor measures the pH at ambient conditions.

24. An optical fiber pH sensor (100), (200), (300) according to claim 1, 5 or 6, wherein the sensor measures pH in pipes and difficult access equipment.

* * * * *